United States Patent [19]

Feaster

[11] Patent Number: 5,578,049
[45] Date of Patent: Nov. 26, 1996

[54] OPTICAL ZONE MARKER FOR REFRACTIVE SURGERY

[76] Inventor: Fred T. Feaster, 4417 Overton Crest, Fort Worth, Tex. 76109

[21] Appl. No.: 315,535

[22] Filed: Sep. 30, 1994

[51] Int. Cl.⁶ ........................................................ A61F 9/00
[52] U.S. Cl. ................................................................ 606/166
[58] Field of Search ............................... 606/166; 33/233, 33/297, 298, 644, 670

[56] References Cited

U.S. PATENT DOCUMENTS

| | | | |
|---|---|---|---|
| 1,582,063 | 4/1926 | McIntosh | 33/233 |
| 3,190,002 | 6/1965 | Bliss | 33/228 |
| 3,325,937 | 6/1967 | Morrow | 42/102 |
| 4,515,157 | 5/1985 | Fedorov et al. | 606/166 |
| 4,679,344 | 7/1987 | Jolly | 42/100 |
| 4,705,035 | 11/1987 | Givens | 606/166 |
| 4,875,767 | 10/1989 | Wright | 351/212 |
| 5,334,213 | 8/1994 | Price, Jr. | 606/166 |

*Primary Examiner*—Michael Powell Buiz
*Assistant Examiner*—Patrick W. Rasche
*Attorney, Agent, or Firm*—Arthur F. Zobal

[57] ABSTRACT

The marker is a hollow cylindrical member having a given height between two opposite ends and a given radius with an opening extending therethrough between the two ends and a central axis extending through the opening. One of the ends is a cornea engaging end and the other end is a viewing end. Two aligned spaced apart pointing members extend radially inward to the central axis of the opening from one side of the member such that when viewed from either end, from the central axis, the two pointing members are radially aligned. The pointing member closest to the viewing end has a width not greater then the width of the other pointing member. In another embodiment, a solid pointing plate is employed instead of the two pointing members.

1 Claim, 3 Drawing Sheets

Prior Art

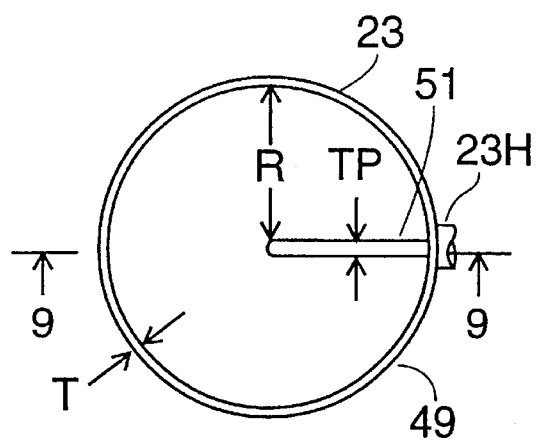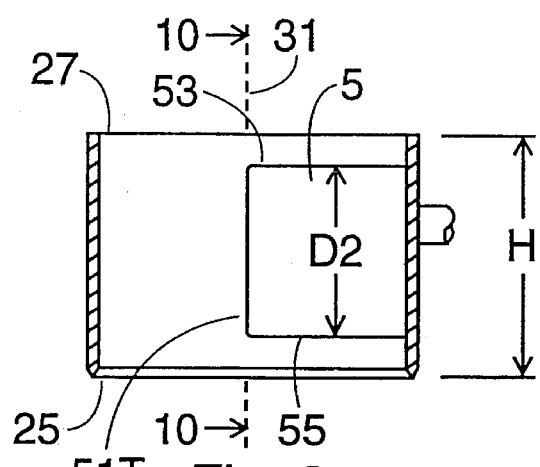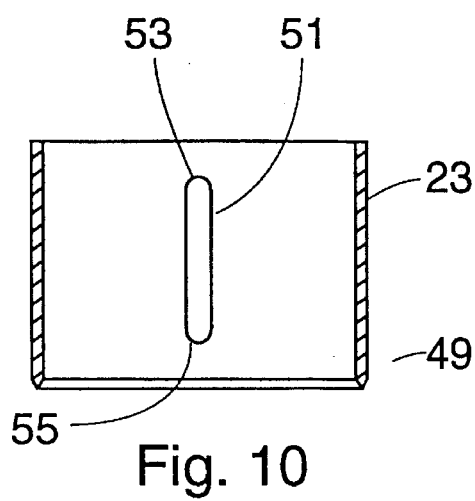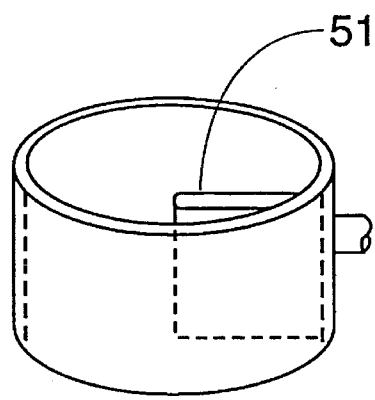
Fig. 8
Fig. 9
Fig. 10
Fig. 11

OPTICAL ZONE MARKER FOR REFRACTIVE SURGERY

BACKGROUND OF THE INVENTION

1. Field of the Invention

The invention relates to a marker for marking the central portion of the cornea which is to remain uncut in radial keratotomy.

2. Description of the Prior Art

Incisional keratotomy, specifically radial keratotomy, and astigmatic keratotomy, are surgical procedures which alter the refractive characteristics of the cornea by making precise incisions in the cornea at specific locations to ultimately produce a specific desired change in the corneal curvature, thereby changing the corneal refractive power. An essential feature of radial and astigmatic keratotomy is the determination of the optical zone, which is the central portion of the cornea which is to remain uncut. Determining and marking the central corneal optical zone is accomplished using an optical zone marker of a desired diameter. The optical zone marker is comprised of a circular cylinder of a somewhat variable vertical height attached to a handle for manipulation purposes (FIG. 1). One end of the cylinder has a sharp pointed edge which is used to encircle and outline the central corneal optical zone when pressed on the corneal epithelial surface. The central optical zone is demarcated either by pressing the optical zone marker edge against the corneal epithelium producing a visible imprint when the marker is removed, or the marker edge is coated with marking ink which leaves an ink imprint on the cornea when pressed against the cornea.

One difficulty, however, in using existing corneal markers, is the problem of assuring that the cornea is visualized, and the central optical zone demarcated while viewing the cornea perpendicular to the long axis of the cylinder of the optical zone marker. Inadvertent off-axis viewing through the optical zone marker may result in accidental decentration of the optical zone demarcation on the cornea which will have the significantly adverse affect of causing the refractive surgery to be performed off center, and therefore, producing a sub-optimal result. Various attempts have been made to ensure that visualization through the optical zone marker is indeed parallel to the long axis of the optical zone marker. These techniques include requiring the surgeon to close one eye while viewing the optical zone marker through the operating microscope, and attempting to view the light reflex off the dome of the cornea in the center of the optical zone marker as best possible. Another means of attempting to ensure proper centration is the incorporation of a single center indicating pointer attached within the optical zone marking cylinder (FIG. 2). Although this additional design feature provides some improvement in centration capability, the operating surgeon is still not assured of visualization through the optical zone marker parallel to the long axis of the optical zone marking cylinder.

Another optical zone design incorporating "cross hairs" (FIG. 3) has also been developed in order to ensure central placement of the optical zone marker on the corneal surface. Again, the cross hairs do not provide for accurate alignment parallel to the long axis of the optical zone marker cylinder.

SUMMARY OF THE INVENTION

In order to alleviate this problem of on-axis visualization, orientation, and marking of the cornea, there is herein presented a new optical zone marker design which incorporates the use of two center pointers, one positioned immediately above the second central pointer in such a way that when the cornea is viewed through the optical zone marker, and the two pointers are seen to be positioned and aligned one on top of the other, then, the orientation of the observer parallel to the long axis of the optical zone marker cylinder is assured. That is to say, by monocular viewing the optical zone marker in such a way that one pointer is seen to be aligned directly on top and overlying the second (lower) pointer, such that the tips and full length of each pointer coincide and completely overlap, then proper alignment parallel to the long axis of the optical zone cylinder is assured. The uppermost pointer has a dimension equal to or very slightly smaller than the underlying pointer (the pointer closest to the corneal surface so that the physical size of the uppermost pointer will not obscure the view and thereby the localization of the lower pointer, preventing alignment of the two pointers. That is to say, the uppermost pointer should be of such a dimension in size so that it does not completely block out visualization of the lowermost pointer.

In a second embodiment, the center indicator pointer comprises a solid plate or blade oriented with a vertical thin edge parallel to the long axis of the optical zone marker, and the uppermost edge perpendicular to this vertical edge. The orientation of this optical zone marker is accomplished by viewing the uppermost edge in orientation with the underlying plate such that the upper edge is seen to be completely aligned with the underlying blade with no observed protrusion or extension of the lowermost aspect of the blade seen, thereby ensuring proper alignment of the optical zone marker.

DESCRIPTION OF SURGICAL PROCEDURE

The following is a description of an anticipated surgical procedure using the newly described optical zone marker:

The patient's operative eye is rendered topically anesthetic and prepped and draped in the usual sterile fashion for refractive surgery. The patient is positioned under the operating microscope and the eyelids separated with an eyelid speculum. The patient is instructed to observe and fixate on the operating microscope fixation light. The optical zone marker of the desired diameter is then oriented overlying the corneal surface in substantial alignment with the central corneal optical zone as determined by a combination of the light reflex from the cornea and the pupil opening location. With the optical zone marker oriented such that the two center indicating pointers are aligned so that the central tips and lengths substantially overlap and correlate in orientation, the optical zone marker is then pressed down such that the center of the cornea immediately underlies the central tip of the indicator. With the optical zone marker in proper alignment and orientation relative to both the observing surgeon and the underlying corneal surface, the optical zone marker is pressed on the corneal surface thereby, demarcating the desired central optical zone which is to be left uncut. The surgical procedure is then continued in the usual fashion for refractive surgery as per the protocol of the operating surgeon.

Thus the optical zone marker of the preferred embodiment has double center indicator pointers oriented and located such that when they are properly aligned, visualization and orientation through the optical zone marker in proper orientation relative to the long axis of the optical zone marker is assured. It is anticipated that this improved design will minimize decentration and misalignment in marking the optical zone of the cornea, thereby providing superior surgical results in refractive surgery.

BRIEF DESCRIPTION OF THE DRAWINGS

FIG. 8 is a top plan view of the optical zone marker of another embodiment of the invention.

FIG. 9 is a cross-sectional view of the FIG. 8 as seen along lines 9—9 thereof.

FIG. 10 is a cross-sectional view of FIG. 9 as seen along lines 10—10 thereof.

FIG. 11 is an isometric view of the marker of FIGS. 8–10.

DESCRIPTION OF THE PREFERRED EMBODIMENT

Figure 1:
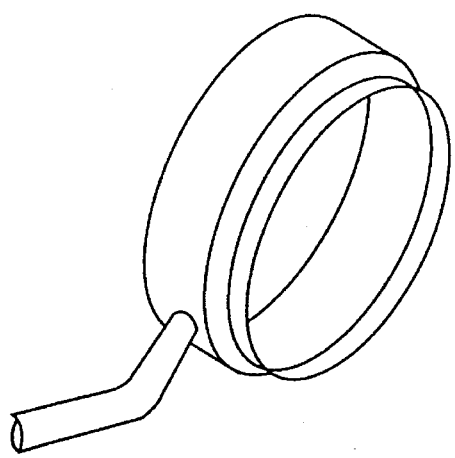
FIGS. 1–3 disclose prior art optical zone markers.
Figure 2:
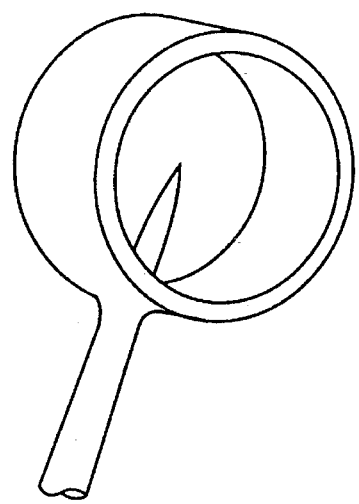
Figure 3:
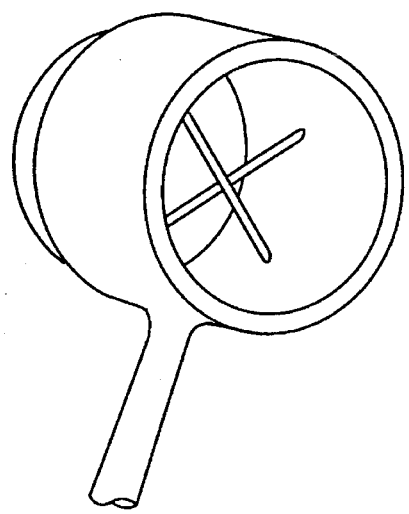
Figure 4:
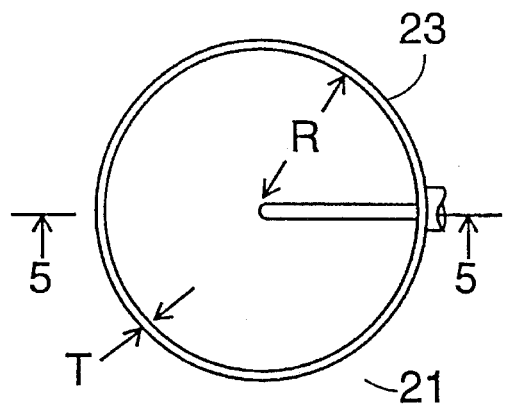
FIG. 4 is a top plan view of the optical zone marker of the preferred embodiment of the invention.
Figure 5:
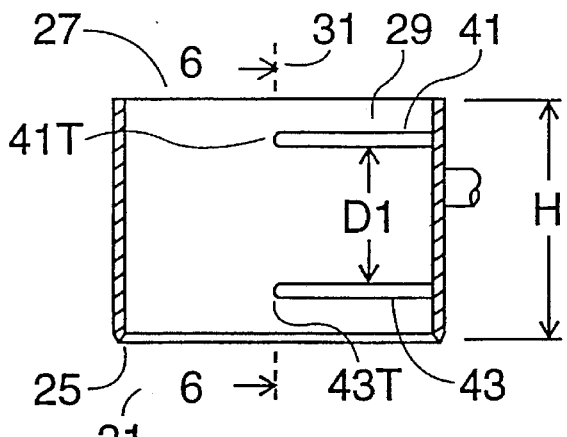
FIG. 5 is a cross-sectional view of FIG. 4 as seen along lines 5—5 thereof.
Figure 6:
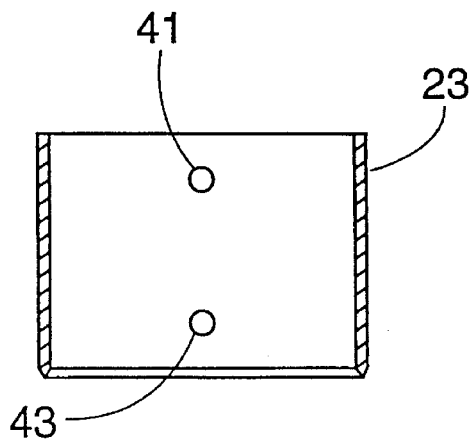
FIG. 6 is a cross-sectional view of FIG. 5 as seen from lines 6—6 thereof.
Figure 7:
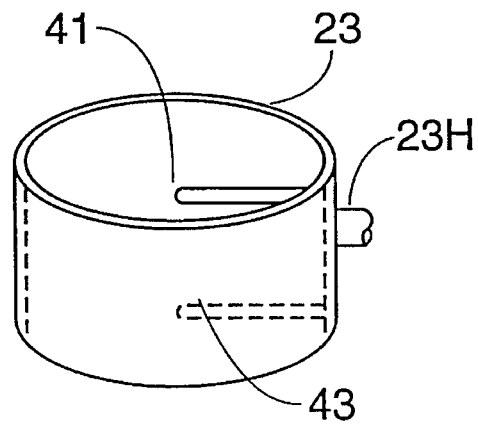
FIG. 7 is an isometric view of the marker of FIGS. 4–6.

Referring to FIGS. 4–7, the preferred optical zone marker is identified by reference numeral 21. It comprises a hollow cylindrical wall 23 having a given height H; a given radius R; and a given wall thickness T. A handle shown partially at 23H is attached to the outside of the wall 23. The marker has a sharp end 25 for engaging the cornea of the eye and an opposite viewing end 27. A central opening 29 extends between ends 23 and 27 with a central axis 31. Two spaced apart pointing members 41 and 43 extend from the inside of the wall 23 to the axis 31 such that they are radially aligned as seen from either end 25 or 27 and their inner tips 41T and 43T coincide with the axis 31. The thickness TM of the members 41 and 43 are the same. As seen in FIG. 6, each of the markers 41 and 43 comprises a cylindrical member. The diameter of member 41 may be somewhat less than that of member 43 but not greater. The members 41 and 43 are spaced apart by a distance D1. The distance of member 41 to end 27 is less than the distance of member 43 to end 25.

In using the marker 21 of FIGS. 4–7, the surgeon views the cornea through the opening at end 27 to center the member 23 by aligning pointers 41 and 43 with their tips 41T and 43T aligned at the desired centerpoint of the cornea and then the marking end 25 is placed against the cornea of the eye to mark the center portion of the cornea to remain uncut.

The device 21 is formed of suitable surgical quality metal. In one embodiment the device 21 may have the following dimensions: H is equal to 2–3 mm.; R is equal to 1.25–5 mm.; T is equal to about 0.5 mm.; D1 is equal to about 1–2mm.; and the diameter of each of the member 41 and 43 is equal to about 0.25–0.5 mm. It is to be understood that these dimensions may vary.

The marker 49 of FIGS. 8–11 is the same as that of FIGS. 1–4 except the pointer comprises a solid rectangular plate 51 extending from the inside of the wall 23 to the central axis 31 with its inner edge or tip 51T coinciding with the axis 31. Its two edges 53 and 55 are radially aligned. The plate 51 has the same thickness TP over its entire area. In one embodiment, the dimensions H, R, and T, may be the same as those of the embodiment FIG. 4–7. TP is equal to about 0.25–0.5 mm. and D2 is equal to about 1–2 mm. It is to be understood that these dimensions may vary. The marker 49 is formed of surgical quality metal.

In using the marker 51, the surgeon views the cornea through the opening at end 27 to center the member 23 by aligning the edges 53 and 55 with the tip 51T located at the desired centerpoint of the cornea and then the marking end 25 is placed against the cornea of the eye to mark the center portion of the cornea to remain uncut.

I claim:

1. An optical zone marker for refractive surgery, comprising:

a hollow cylindrical member having first and second opposite ends, a given height between said first and second ends, an opening extending therethrough between said first and second ends with said opening having a given radius, and a central axis extending through said opening, said first end being an engaging end for engaging the cornea of the eye and said second end being a viewing end, a pointing plate extending radially inward to said central axis of said opening from one side of said cylindrical member, said pointing plate having an inner edge coinciding with said central axis and a transverse edge located closer to said viewing end than to said engaging end, with said transverse edge being perpendicular to said inner edge, said pointing plate having a dimension along said height of said cylindrical member which is greater than at least one half of said height of said cylindrical member, said pointing plate has substantially the same thickness over its entire area.

said pointing plate has an edge spaced from said transverse edge with said transverse edge and said edge spaced from said transverse edge being spaced from said first and second ends.

* * * * *